United States Patent [19]

Abboud et al.

[11] Patent Number: 4,880,931

[45] Date of Patent: Nov. 14, 1989

[54] ACRYLOXY-CONTAINING COMPOUNDS

[75] Inventors: George E. Abboud, Ajax, Canada; Christopher H. Such, Mount Eliza, Australia; Susan M. Horley, Loudwater; Julian A. Waters, Goring-On-Thames, both of England

[73] Assignee: Imperial Chemical Industries PLC, London, England

[21] Appl. No.: 218,278

[22] Filed: Jul. 13, 1988

Related U.S. Application Data

[63] Continuation of Ser. No. 815,313, Jan. 2, 1986, Pat. No. 4,783,539, which is a continuation of Ser. No. 436,355, Oct. 25, 1982, abandoned.

[30] Foreign Application Priority Data

Oct. 23, 1981 [GB] United Kingdom ................ 8132086
Apr. 30, 1982 [GB] United Kingdom ................ 8212639

[51] Int. Cl.$^4$ .................. C07D 233/36; C07D 239/10
[52] U.S. Cl. ..................................... 544/316; 548/320
[58] Field of Search ......................... 548/320; 544/316

[56] References Cited

U.S. PATENT DOCUMENTS 4,319,032 3/1982 Sandri et al. ........................ 548/320

Primary Examiner—Richard A. Schwartz

Attorney, Agent, or Firm—Cushman, Darby & Cushman

[57] ABSTRACT

Polymerizable monomers of structure

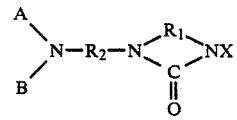

wherein $R_1$ and $R_2$ are $C_{2-3}$ alkylene groups, the same or different; A and B are substituted $C_{2-18}$ alkyl groups at least one group A or B comprising in a substituent a polymerizable ethylenically unsaturated group; ane $X=H$, $C_{1-18}$ alkyl or

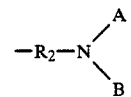

the monomers being substantially free from non-polymerizable water-soluble contaminants; processes of manufacture and derived polymers including copolymers; and aqueous polymer dispersions, their manufacture and use in coatings including paints.

7 Claims, No Drawings

ACRYLOXY-CONTAINING COMPOUNDS

This is a division of application Ser. No. 815,313, filed Jan. 2, 1986, now U.S. Pat. No. 4,783,539, which is a continuation of Ser. No. 436,355 filed Oct. 25, 1982, now abandoned.

This invention relates to polymerisable nitrogen-containing monomers and to their preparation; to polymers based on these monomers; to stable, water-dilutable dispersions of polymer particles and to their preparation; and to coating compositions, for example paints, which comprise the polymer.

The invention relates more specifically to polymerisable monomers, and polymers based on these monomers, which contain a cyclic ureido group having the structure

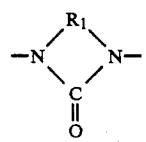

wherein $R_1$ is an alkylene
group containing 2 or 3 carbon atoms.

When $R_1$ is $(CH_2)_2$ the group is also known as an ethylene urea or imidazolidinone group. In this specification we use the term 'cyclic ureido' group to denote the above structure except where a more precise definition is required for a specific monomer.

It is known, for example from British Pat. Nos. 1,061,942 and 1,072,894, that polymerisable monomers containing the cyclic ureido groups are useful in the preparation of polymers having good adhesion to a substrate, particularly under wet conditions. However, many of the monomers which have been proposed for use in the preparation of such polymers require a lengthy and complicated manufacturing process; some are sensitive to hydrolising conditions; they cannot be prepared in a 'clean' state; and they cannot be freed easily from contaminants produced during manufacture. Some of the contaminants of the prior monomers even detract from those properties in the polymer which are specifically sought in using the prior monomers; for example non-polymerisable water-soluble contaminants. In U.S. Pat. No. 4,319,032, for example, are described methods of preparing certain monomers by reacting an omega-amino-alkyl or substituted alkyl alkylene urea with an unsaturated glycidyl ether or ester. It is clear from the worked Examples and from the teaching of the patent that the monomers produced by these methods are not eminently suitable in the preparation of polymers, particularly polymer latices, and especially acrylic polymer latices, which are to be used in water-based paints. The products are highly viscous (see Example 6) and contain non-polymerisable water-insoluble and other impurities, particularly those products which have involved the co-reaction with an unsaturated glycidyl ester such as glycidyl methacrylate. In this invention we provide polymerisable monomers containing a cyclic ureido group which have advantages over those just described. The monomers can be prepared in high yield using simple reaction conditions and they are free from deleterious contaminants. They can be used to produce polymers, polymer dispersions and coating compositions which have improved properties, particularly compositions which comprise an acrylic polymer dispersion.

The structure of the monomers can be widely varied to include, as well as a polymerisable ethylenically unsaturated group of a desired type, one or more more other types of functionality. The hydrophiliclyophilic balance may also be widely varied so that the monomer may be water-soluble at an extreme and water-insoluble at the other. Unlike many prior art monomers containing an amino group, the monomers provided by this invention yield polymers which do not exhibit undesirable yellowing during use. Furthermore the monomers can be specifically designed to be stable against hydrolysis and aminolysis.

According to this invention we provide a polymerisable monomer of structure

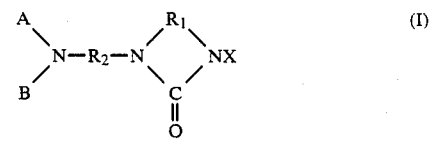 (I)

wherein $R_1$ and $R_2$ are alkylene groups containing 2 or 3 carbon atoms, the same or different; A and B are substituted $C_{2-18}$ alkyl groups, the same or different, which are each linked to the nitrogen atom through a carbon atom at least one of said groups A and B comprising in a substituent at least one polymerisable, ethylenically-unsaturated group; and $X = H$, $C_{1-18}$ alkyl or

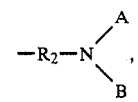

the
said monomer being substantially free from non-polymerisable water-soluble contaminants.

The invention also provides an addition polymer which comprises a monomer residue of structure

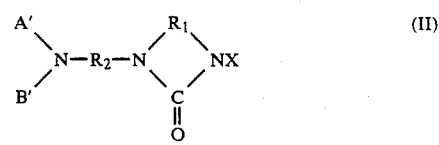 (II)

wherein $R_1$ and $R_2$ are alkylene groups containing 2 or 3 carbon atoms, the same or different; $X = H$, $C_{1-18}$ alkyl or

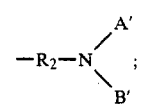

and either group A' or B' is the same as group A or B respectively as defined above and the remaining group A' or B' is an addition polymer residue of group A or B as defined above or both of groups A' and B' are addition polymer residues of the groups A and B as defined above, the said polymer being substantially free from non-polymerisable water-soluble contaminants.

The invention further provides an addition polymer which has been prepared by the polymerisation of monomers which comprise at least 0.1% by weight, based on the total weight of the monomers, of a monomer as defined above.

The invention also provides an addition polymer which has been prepared by polymerising monomers which comprise at least one monomer comprising a group reactive with a secondary amine, the said reactive group having been reacted during or following polymerisation with a secondary amine of structure

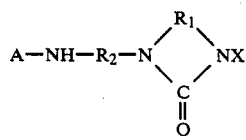

wherein A, $R_1$, $R_2$ and X are as defined above. Monomers comprising a group reactive with the secondary amine include glycidyl (meth)acrylate and allyl glycidyl ether.

It is well known that the presence of a cyclic ureido group can give enhanced water-resistance properties to a polymer and to mixtures of polymers and that the cyclic ureido group may be incorporated within a polymer by the use of a copolymerisable monomer which includes the cyclic ureido group. Surprisingly, in view of the problems associated with the preparation of many prior monomers of this type we have found that monomers of structure (I) above can be made readily at relatively low temperatures by processes which are described below. In order to achieve the variations in hydrophilic-lyophilic balance, solubility, functionality and polymerisation characteristics which are referred to above, the nature of groups A and B may be varied widely by variations in these processes.

A substituent in the $C_{2-18}$ alkyl groups of groups A & B may be, for example, a hydroxyl group and/or a group which comprises a saturated or unsaturated hydrocarbon group optionally linked to the alkyl group through a hetero atom, for example oxygen.

In an important embodiment of the invention, group A and/or group B is a substituted propyl group of structure

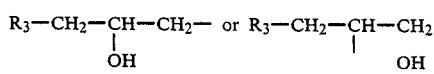

wherein the substituent $R_3$ comprises a polymerisable ethylenically unsaturated group selected from allyl, allyloxy, (meth)acryloxy, vinyl or vinyloxy or a non-polymerisable group selected from $C_{1-18}$ alkyl or substituted alkyl, aryl or substituted aryl. The alkyl substituent may be for example hydroxy or halogen such as chloro. The aryl group may be phenyl.

Alternatively, group A and/or group B may be a substituted ethyl group of structure

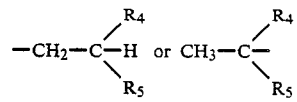

where $R_4$ is H, or $C_{1-18}$ alkyl and where $R_5$ is selected, for example from alkyl or aryl carboxy, allyl carboxy, amido, carboxy, chloro or cyano.

In a further embodiment groups A or B may be

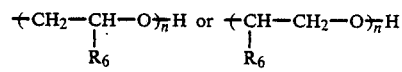

wherein $R_6$ =H or $C_{1-18}$ alkyl and n =1-100

Similarly the intermediate secondary amine of formula III above from which the monomers of this invention may be readily and conveniently prepared, can have wide variation in the composition of the group A. However in the important embodiment group A has the structure

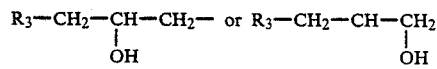

wherein $R_3$ is as described above. Alternatively group A may have the structure

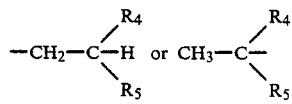

wherein $R_4$ and $R_5$ are as described above. Preferred secondary amine structures exclude ester linkages which would introduce vulnerability to aminolysis or hydrolysis in the presence of primary amine. Such preferred secondary amines can be readily prepared in a high state of purity, free from deleterious by-products, and they in turn can be used under mild reaction conditions to prepare monomers of our invention to a good level of purity, again free from deleterious by-products. Preferred secondary amines are those where $R_3$ is for example allyl, allyloxy methyl, ethyl, propyl, butyl or higher alkyl, phenyl or substituted phenyl, hydroxymethyl and other hydroxy alkyl, chloromethyl and other halogenated alkyls, vinyl or vinyloxy groups or alternatively where $R_5$ is amido, chloro or cyano.

Specific monomers of this invention can be polymerised to provide homopolymers or can be copolymerised with other specific monomers of this invention. Alternatively monomers of this invention can be copolymerised with other polymerisable ethylenically unsaturated compounds to form copolymers. Polymers of this invention include at least 0.1% of a monomer of formula I above of this invention and suitable comonomers may also include for example allyl alcohol, allyl glycidyl ether, allyl methacrylate, acrylonitrile, acrylamide, methyl or higher alkyl acrylates or methacrylates, maleic anhydride or maleic esters, styrene or substituted styrene, vinyl acetate, vinyl chloroacetate, vinyl chloride, vinylidene chloride, vinyl bromide, vinyl methyl ether, vinyl propyl ether, vinyl butyl ether, vinyl benzoate, vinyl laurate, vinyl methoxyethyl ether, vinyl benzyl ether, vinyl sulphonic acid, vinyl pyrrolidone, vinyl pyridine, methacrylonitrile, methacrylamide, ethylene and higher olefins.

It will be appreciated that the homopolymers and copolymers of this invention may be mixed and used with other polymers.

We also provide a process of preparing an intermediate of structure

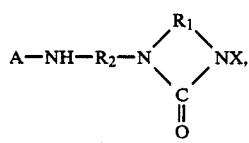  (III)

wherein a primary amine of structure

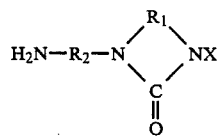  (IV)

is reacted in the presence of a solvent with a material comprising an epoxide group, the said material having a structure to provide group A after reaction with the primary amino group; $R_1$ and $R_2$ being alkylene groups containing 2 or 3 carbon atoms, the same or different; and $X = H$, $C_{1-18}$ alkyl or $-R_2-NH_2$. Preferably A is derived from a material comprising an epoxide group which does not react by the Michael addition reaction with an unsaturated double bond. For example an allyl group may be present but a (meth)acrylate group is preferably absent. We also provide a process of preparing an intermediate as defined in (III) above, wherein a primary amine of structure (IV) is reacted by the Michael addition reaction with a material having an activated double bond.

We have found that using either of these techniques, the secondary amines (III) may be readily and conveniently prepared and is illustrated as follows. Amino ethyl imidazolidinone is dissolved in a solvent preferably water or more preferably a $C_{1-14}$ alkanol and stirred at ambient temperature. A monofunctional epoxide compound is added; the mix is stirred and held below 40° C. for 3 hours. Two phases may be present initially but the product is either a clear homogeneous solution or is a micellar dispersion depending on the composition of the monofunctional epoxide.

The product from the reaction is easily checked for unreacted epoxide by determining the epoxide value. Other solvents or solvent mixtures may be used but water and preferably a $C_{1-14}$ alkanol is a preferred solvent because then the reaction proceeds quickly and is easily monitored. We find that secondary amines having a variety of functional groups including, optionally, allyl ether groups can be made by selecting reactive materials which include the functional groups in addition to the epoxide group. Secondary amines (III) having more than one additional functional group can be made and compounds with more than one epoxide can be used. Alternatively, we find that the secinary amine (III) can be made readily by adding materials with certain activated double-bonds to an aqueous solution of amino ethyl imidazolidinone. Preferred secondary amines are made by selecting materials which do not include an ester linkage. We find that when such a linkage is present the resulting secondary amines are less suitable for the preparation of some cyclic ureido compounds which do not contain an unsaturated olefinic group. For example preferred secondary amines can be made using ethylene oxide, propylene oxide, butylene oxide, allyl glycidyl ether, glycidol, epichlorhydrin, acrylonitrile or methacrylonitrile. When secondary amines are made with glycidyl acrylate, glycidyl methacrylate, glycidyl "Versatate", allyl methacrylate, methyl acrylate and other esters of acrylic or methacrylic acid, acrylamide or methacrylamide, the product is likely to contain con-polymerisable water-soluble contaminants.

We also provide a process of preparing a monomer of structure I substantially free from non-polymerisable water-soluble contaminants wherein an intermediate material of structure

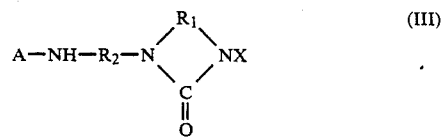  (III)

as defined above is reacted with a material comprising an epoxide group the said material having a structure to provide group B after reaction with the amino group. Preferably the material comprising an epoxide group which has a structure to provide group B is selected from glycidyl (meth)acrylate, or allyl glycidyl ether.

We have found that this process may be readily and conveniently carried out using techniques similar to those employed when preparing the secondary amines. In a typical preparation an epoxide compound is added to an aqueous solution of the secondary amine and the temperature raised to 50°-60° C. and maintained for approximately 3 hours. Two phases may be present initially but the product is either a clear homogeneous solution or is a micellar dispersion depending on the combination of the epoxide reagent.

The product from the reaction is easily checked for unreacted epoxide by determining the epoxide value. Other solvents or solvent mixtures may be used but water and/or a $C_{1-14}$ alkanol are preferred solvents because the reaction proceeds easily and can be readily monitored. The epoxide can optionally include an ethylenically unsaturated group or some other functional group or groups, but since the secondary amine does not normally comprise an ethylenically unsaturated group such as a (meth)acrylate group this has to be included in the epoxide compound. For example the epoxide compound can be allyl glycidyl ether or other epoxy alkyl allyl ether, but preferably glycidyl acrylate or glycidyl methacrylate or other epoxy alkyl acrylate or methacrylate. Alternatively, for example the epoxide compound can be ethylene oxide or higher alkyl oxide, benzyl epoxide, epichlorhydrin, an epoxy resin, glycidol, the glycidyl ester of "Versatic" acid or other glycidyl ethers.

Although the range of structures for our monomer (I) which can be made using the simple processes just described above is very wide, the scope of the monomer I is in no way limited by these processes. The desired and useful characteristics of the monomer compounds of our invention arise from the structure of the monomer itself and not from the process of preparation.

The monomers of this invention may include, for example, halogen or cyano groups which may be intended to modify certain physical properties of derived polymers or such groups may be intended to participate in further chemical reactions after polymer formation, e.g. hydroxyl or allyl groups. Alternatively the monomer compounds may be readily designed to be fully water-soluble or to be surface-active in aqueous media or to be water-insoluble depending on their final use.

According to a further aspect of this invention we provide a water-dilutable dispersion of polymer particles substantially free from non-polymerisable water-soluble contaminants, the particles comprising an addition polymer which comprises a monomer residue having the structure

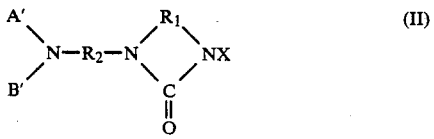

as defined above. Preferably the addition polymer comprises at least 25%, more preferably at least 50% by weight of acrylic comonomers.

We also provide a process for preparing a water-dilutable dispersion of polymer particles as defined above wherein there is polymerised in water and/or in a water-miscible liquid, ethylenically unsaturated monomers which comprise at least one monomer of structure

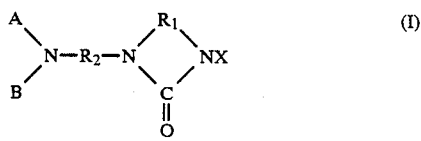

as defined above.

We also provide a further process for preparing the dispersion of polymer particles defined above wherein there is polymerised in water, and/or in a water-miscible liquid ethylenically unsaturated monomers which comprise at least one monomer comprising a group reactive with a secondary amine, the said reactive group being reacted, either during or following polymerisation of the monomers, with a material of structure

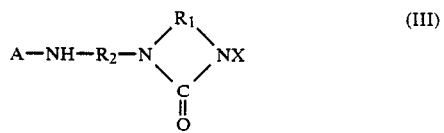

wherein $R_1$ and $R_2$ are as defined above and where A is a substituted alkyl group linked to the adjacent nitrogen atom through a carbon atom.

The invention also provides a water-dilutable coating composition which comprises a water-dilutable dispersion of polymer particles as defined above, and a water-based paint which comprises a dispersion of polymer particles as defined above.

We also provide a water-based paint which also comprises polymer particles comprising a further polymer free from residues of the monomer I.

The water-dilutable dispersions of polymer particles of this invention may have polymer contents from as low as 5% up to 80% by weight based on the total weight of dispersion. However, low solids dispersions may give rise to difficulty when preparing coating compositions such as paints with appropriate viscosity for application by brush or roller whilst very high solids dispersions may be difficult to handle and may display variable viscosity during storage. It is preferred that the polymer content is in the range 45% to 60% by weight based on the total weight of the dispersion. The polymer particles are usually substantially spherical but the polymer particles in the dispersions of this invention are not restricted as to shape. For example, the particles may resemble clusters of smaller particles or they may be ellipsoidal. Particle size may be varied within a wide range. The distribution of sizes may be wide or narrow. Usually the mean particle size is greater than 0.05 micron but less than 10 microns in diameter and preferably is less than 1 micron in diameter.

The dispersions of this invention are water-dilutable, that is the liquid or liquid mixture constituting the continuous phase is fully miscible with water.

Suitable liquids which may constitute the continuous phase include water, methanol, ethanol, isopropanol, acetone and ethylene glycol. Mixtures of these liquids may be employed. The liquids may contain dissolved salts. Municipal mains water may be used.

The polymer composition can be varied widely. Suitable ethylenically unsaturated comonomers which can be used in the preparation of the polymer dispersions include allyl alcohol, allyl glycidyl ether, allyl acrylate, allyl methacrylate, acrylonitrile, acrylamide, methyl or higher alkyl acrylates or methacrylates, maleic anhydride or maleic esters, styrene or substituted styrene, vinyl alcohol, vinyl acetate, vinyl chlorooacetate, vinyl chloride, vinylidene dichloride, vinyl bromide, vinyl methyl ether, vinyl propyl ether, vinyl butyl ether, vinyl benzoate, vinyl laurate, vinyl methoxyethyl ether, vinyl benzyl ether, vinyl sulphonic acid, vinyl pyyrolidone, vinyl pyridine, methacrylonitrile, methacrylamide, ethylene and higher olefins. Difunctional or higher functionality monomers may be included, for example ethylene glycol dimethacrylate, poly(ethylene oxide)-dimethacrylate or divinyl benzene. The defined monomer residue I according to the invention is usually included at a relatively low level in the defined polymer and preferably is present in a proportion of 0.1% to 5% by weight based on the total weight of polymer.

The polymer may have any suitably average molecular weight provided that it is sufficiently high to permit a distinct particle phase rather than it remain in solution. Preferably the molecular weight of the polymer of the disperse particles is greater than 10,000 and it may be very high, for example up to several million. At one extreme the polymer may be crosslinked so that each particle comprises a single crosslinked polymer chain and the particles are then gel particles.

The water-dilutable dispersions of this invention may include any of the ingredients commonly used in emulsion polymerisation processes, for example emulsifiers and surfactants, and these may include both non-ionic and ionic materials. Water-soluble polymers may be included for example those commonly referred to as "protective colloids" such as hydroxy ethyl cellulose, poly(vinyl acetate/vinyl alcohol), poly(vinyl pyrrolidone), poly(acrylamide) and sodium carboxy methyl cellulose. Surfactant-type polymeric species may also be present for example block or graft copolymers or polymeric species which may be formed "in-situ" during the process of preparing the water-dilutable dispersion.

Transfer agents such as thioglycollic acid primary octyl mercaptan and other mercaptans may be included to lower and control the molecular weight of the polymer. The dispersion may also include materials which modify the properties of the dispersions or of the subsequently derived coating compositions, for example plasticising agents or coalescing agents. Other additives may include anti-foam agents, biocides and means for adjusting the pH.

The water-dilutable dispersions of polymer particles of this invention may be combined with other polymers. These other polymers may be soluble or insoluble in the water-dilutable continuous phase of the dispersion and may or may not contain the monomer residue which is defined above. Where polymers are combined in this way the proportion of the above defined monomer residue which is present should not be less than 0.1% by weight based on the total weight of polymer and preferably should not be less than 1% by weight.

The water-dilutable dispersions of this invention are particularly useful since they yield coating films which have good adhesion to a substrate. This can be shown by a suitable experimental comparison of a coating film prepared from a dispersion which does not contain the above defined polymer residue but is otherwise very similar. When the polymers of dispersions to be compared have a composition such that the particles will coalesce at room temperature, thin polymeric films can be made by pouring some of each dispersion onto a substrate to produce a thin fluid layer and allowing the diluent phase to evaporate. Subsequently the water-sensitivity of the film and its adhesion performance after the film has been soaked in water may be assessed using simple laboratory tests. For example, the rate at which blisters appear and the ease with which the film is torn off from the substrate by contacting the surface with sticky tape and pulling away from the substrate can be compared. Even where the above-defined monomer residue is present at only 1 or 2% by weight based on the total weight of polymer the dispersions of this invention show markedly improved performance under these tests compared to the dispersions which do not contain the defined monomer residue. Similarly if the polymer composition is such that an elevated temperature is required to promote particle coalescence, comparisons of film water sensitivity show that the performance is markedly better for dispersions of the present invention. The improvement in the performance is especially marked when the substrate has a coating derived from an alkyd-based paint, the films from the prior dispersions generally showing very poor adhesion performance which is commonly referred to as "wet adhesion".

Water-dilutable dispersions of polymer particles which comprise monomer residue as defined above may be prepared using any of several known "emulsion polymerisation" techniques. These include simple "one-shot" processes in which a mixture of monomers, including the monomer II defined above, emulsifier or surfactant, water and/or water-dilutable liquid and free-radical initiator is raised in temperature, to give controlled decomposition of the initiator. Polymerisation proceeds and polymer particles, representing a third phase distinct from the water and monomer phase, are produced. The particles are stabilised against flocculation and aggregation by adsorbed emulsifier or surfactant molecules and usually also by the ionic residues remaining after the decomposition of the initiator. The monomer phase is eventually consumed and the product is a water-dilutable dispersion of particles. When producing dispersions of high polymer content, that is greater than 25% by weight of polymer based on the total weight of dispersion, a "seed and feed" process is usually adopted. In this process, a small proportion of the total monomer is polymerised in the presence of emulsifier or surfactant to form a dilute dispersion of seed polymer. Subsequently polymerisation is continued with the remainder of the monomer added as "feed" usually over a few hours during which time the size of existing particles may increase and some new particles may be formed. Additional initiator and/or emulsifier or surfactant may be added during this stage. The product is a high solids, water-dilutable dispersion. Alternatively the monomer may be emulsified in water and this emulsion used as feed. In further known variations of the process, a water-soluble polymer, referred to as a "protective colloid" is dissolved in the water phase before commencing polymerisation. The "protective colloid" has a complex multifunctional role and, for example, contributes to the stability and rheology of the resulting dispersion of polymer particles.

In one process according to this invention a monomer of structure I is dissolved in a solvent which is water-miscible. Suitable solvents include water, methanol, ethanol, acetone and ethylene glycol. The monomer solution is fed to the site of polymerisation during the process. In an alternative process a solution of the monomer of structure I in a solvent which is miscible with the mixture of other monomers is used. Suitable solvents include for example isopropanol and higher alcohols, esters such as ethyl acetate and butyl acetate, ketones, toluene and higher aromatic hydrocarbons. In this alternative process the monomer solution is mixed with all or part of the remaining monomer mixture before this mixture is added to the site of polymerisation. We have found that it is generally easier to store and handle the monomers of structure I as solutions. For aqueous solutions of the monomer it is preferred that the concentration of monomer is between 20 and 50% by weight based on the total weight of the solution. With monomer solutions in organic liquid it is preferred that the concentration of monomer be between 30 and 70% by weight based on the total solution weight. Direct contact between the monomer solution and the initiator, prior to addition to the polymerisation site should be avoided. In a preferred process the monomer of structure I is added, by one of the two methods above, only with the last 50%, preferably not more than the last 25% of the monomer feed. We believe, but are in no way confined to this belief, that by using this technique more of the monomer comprising the defined monomer residue is located at the surface of the polymer particles. However, where the monomer of structure I does not have favourable copolymerising characteristics with the other monomers an alternative process is preferred in which the monomer of structure I is added to the diluent phase at the site of polymerisation before polymerisation is commenced. For example when the monomer of structure I has an allyl functional group as the sole ethylenically unsaturated group and the other monomers are methacrylate esters this alternative process is preferred.

If desired, the composition of the total monomer feed may be altered when the monomer of structure I is to be incorporated so that, for example, it becomes a part of a polymeric component of the particles which is more flexible or more hydrophilic. Thus the amount of plasticising comonomer or a hydrophilic comonomer respectively would be increased during the time the monomer of structure II was added to the polymerisation site.

As previously mentioned, the water-dilutable dispersion of polymer particles of our invention can be made by a process wherein the defined monomer residue is produced either in-situ during the polymerisation process or by a subsequent step. In an alternative process there is included in the monomer mixture at least one reactive monomer which can be concurrently or subsequently reacted with a secondary amine. Preferably the reactive monomer includes an epoxy group but other suitable reactive groups may be present. During the polymerisation process or subsequent to polymerisation and particle formation, a compound of structure (III) as defined above is added and the conditions adjusted so that it reacts with the monomer residue of the reactive monomer to provide a monomer residue of structure (II) where at least one of groups A' and B' comprises a carbon-carbon linkage which is part of the polymer chain. When the water-dilutable dispersions are prepared by this alternative process, the conditions should be selected such that the amount of compound (III) which remains unreacted is at a minimum. This may be assisted by holding the reacting mixture at a temperature above room temperature, for example at 50° C., for about an hour. It is preferred that the reactive monomer is present in excess over the compound (III).

The water-based paints of this invention are mixtures of the above-described water-dilutable dispersions of polymer particles with water-dilutable dispersions of pigment, often termed "mill-bases". The mill-bases may include inorganic pigments such as titanium dioxide; other inorganic particulate material such as calcium carbonate, silica, and clay; water-soluble polymers such as substituted cellulose, methacrylic acid or acrylic acid copolymers and wetting and dispersing agents may be included. The mill-base can be prepared using any of the several techniques known to those skilled in the art. These techniques involve a dispersing or grinding process which separates the particles of the particulate materials in the presence of dispersing agents to give a fluid, stable dispersion. Many other compounds may be added to the paints in order to make contributions to desired paint properties. For example water-soluble polymers and chelating agents may be added to adjust rheology and give improved application properties. Compounds may be added to assist film formation, to promote plasticisation, resistance to freezing, resistance to biological infection and deterioration or to reduce foaming during application.

The paint formulations may be selected so that primer, flat, semi-gloss or gloss paints are produced, and they can be designed to be suitable for both interior and exterior use. By selecting harder compositions for the polymer in the water-dilutable dispersions of polymer particles, paints may be formulated which after drying at elevated temperature give hard, durable films.

The paints of this invention exhibit markedly improved performance in some important property areas which is due to the presence of the defined monomer residue. This can be easily demonstrated by preparing another water-dilutable dispersion which does not include the defined monomer residue but which is otherwise similar to the dispersion of this invention which is under test. The two dispersions are separately mixed at the same proportion with a mill-base to produce two paints. The paints may be assessed and compared in respect of water-resistance properties by using a variety of well accepted tests. For example the "wet adhesion" of the paint films can be assessed with a Gardner Scrub machine using a standard test; the films may be assessed for resistance to blistering, softening-back and time taken to recover when exposed to warm, high humidity conditions; and comparisons of blistering and loss of adhesion to different substrates can be made after immersing the painted substrates in water after the films have been aged for a set time. Even where the defined monomer residue is incorporated at a low level in the water-dilutable dispersions we have found that the paints have surprisingly marked improvements in performance under these tests.

The invention is illustrated by the following Examples in which parts and percentages are by weight.

EXAMPLE 1

Preparation of a monomer of structure I wherein A = hydroxybutyl and B = methacryloxyhydroxypropyl (a) A secondary amine was first prepared by reacting 1,2-epoxy butane with amino ethyl imidazolidinone. The latter is a known compound which may be prepared by reacting diethylene triamine with urea.

| Formulation | | Parts |
|---|---|---|
| X: | Amino ethyl imidazolidinone | 905 |
|    | distilled water | 589 |
| Y: | 1-2, epoxy butane | 500 |

(b) The secondary amine resulting from (a) was reacted with glycidyl methacrylate.

| Formulation | Parts |
|---|---|
| Secondary amine solution (from (a).) | 1550 |
| Distilled water | 300 |
| Glycidyl methacrylate | 774 |

The apparatus used was the same as in (a). The reagents were charged to the flask and stirred. Two phases were apparent. The temperature was raised and maintained at 55°–60° C. for 3 hours with stirring. The product was a clear homogeneous solution. A sample of the product showed no phase separation when diluted with excess water.

Characterisation by NMR indicated that the product was a tertiary amine of structure I in which group A was a hydroxy butyl group and group B was methacrylyloxy, hydroxy propyl group, substantially free from impurity.

EXAMPLE 2

Preparation of a monomer of structure I wherein A = cyano-ethyl and B = methacryloxyhydroxy propyl (a) A secondary amine was first prepared by reacting acrylonitrile with amino ethyl imidazolidinone.

| Formulation | | Parts. |
|---|---|---|
| X: | Amino ethyl imidazolidinone | 129 |
|    | distilled water | 182 |
| Y: | Acrylonitrile | 53 |

A round-bottom flask fitted with a condenser, magnetic stirrer and thermometer was employed, and temperature control was effected by placing the flask in an electrically-heated water-bath to which ice could be added as necessary. Mixture X was stirred until homogeneous. Y was added over 1 hour during which time the temperature was not allowed to exceed 25° C. The temperature was then raised and maintained at 30° C. for a further 4 hours. finally the temperature was raised and maintained at 80° C. for 1 hour with inert gas bubbling through the solution. The effluent gas stream was bubbled through dilute sodium hydroxide solution. Characterisation by NMR indicated that the product was a secondary amine of structure (III) in which A was a cyano ethyl group.

(b) The product from (a) was reacted with glycidyl methacrylate.

| Formulation | Parts |
|---|---|
| Solution from Part (a) | 138 |
| Glycidyl methacrylate | 55 |

The same apparatus was used as in (a). The reagents were charged to the flask and with stirring the temperature raised to and maintained at 50° C. for 4 hours. The product was a clear homogeneous solution. When a sample was diluted excessively with water, no phase separation was apparent.

NMR characterisation indicated that the product was a tertiary amine of structure I in which A was a cyano ethyl group and B was a methacrylyloxy, hydroxy propyl group, substantially free from impurity.

EXAMPLE 3

This was similar to Example 1 except that isopropanol was used as diluent in (a) and (b) in place of distilled water. The product was a clear homogeneous solution in isopropanol.

EXAMPLES 4–6

These Examples were similar to Example 1 except that in (a) various reagents were used in place of the epoxybutane (reagent Y).

| Example No. | Reagent Y | Parts |
|---|---|---|
| 4 | Propylene oxide | 402 |
| 5 | Allyl glycidyl ether | 790 |
| 6 | Glycidol | 513 |

In each Example the product was a clear homogeneous solution, substantially free from impurity.

EXAMPLE 7

Preparation of a monomer of structure I wherein A is derived from the "Versatic" acid ester of glycidol and B is methacryloxyhydroxypropyl (a) The "Versatic"* acid ester of glycidol (molecular weight approx. 242) was reacted with amino ethyl imidazolidinone.
(* Registered Trade Mark of Shell).

| Formulation | | Parts |
|---|---|---|
| X: | "Versatic" acid ester of glycidol. | 250 |
|    | Amino ethyl imidazolidinone | 129 |
| Y: | Distilled water | 20 |

A round-bottom flask fitted as for Example 1 was used.

Mixture X was homogenised by raising the temperature to 40° C. and stirring. Y was added and the mixture maintained at 40°-50° C. for 3 hours. The product at this stage was not water-soluble but gave a clear homogeneous solution when diluted with dilute aqueous hydrochloric acid indicating that the epoxy compound had been consumed. "Versatic" acid is a $C_{8-10}$ α-tertiary carbon carboxylic acid.

| (b) Formulation | Parts |
|---|---|
| Solution from (a) | 246 |
| Glycidyl methacrylate | 88 |

The same apparatus was used in Part I, and the reactants were raised to 50° C. for 2½ hours. A sample of the product gave a clear homogeneous solution when diluted with dilute aqueous hydrochloric acid. When this solution was neutralised an emulsion was produced having some self-stability.

EXAMPLE 8

In this Example a mixture of amines, which included a monomer of structure I, was produced by reacting aminoethyl imidazolidinone with glycidyl methacrylate.

| Formulaton | | Parts |
|---|---|---|
| X: | Amino ethyl imidazolidinone | 905 |
| | Distilled water | 589 |
| Y: | Glycidyl methacrylate | 1,145 |

The apparatus used was the same as for Example 1. Mixture X was stirred until homogeneous. Y was added and the temperature maintained at 30° C. for 3 hours. The temperature was raised to 50°-60° C. for a further 3 hours.

The product was a clear homogeneous solution. A sample, diluted with excess water, showed no phase separation indicating complete reaction of the epoxy compound. NMR characterisation indicated that the product was a mixture of amines some of which contained a methacrylate group, some of which contained a methacrylamido group. The latter will remain as an unpolymerised water-soluble impurity if the product of this Example is copolymerised in aqueous medium with other monomers to produce a dispersion of polymer particles.

EXAMPLE 9

This Example was the same as Example 1 except that allyl glycidyl ether (790 parts) was used in (a) as reactant Y and allyl glycidyl ether (621 parts) was used in (b) instead of glycidyl methacrylate.

EXAMPLE 10

This Example was the same as Example 1 except that allyl glycidyl ether (621 parts) was used in (b) instead of glycidyl methacrylate.

EXAMPLE 11

In this Example a polymer was made using the monomer from Example 3.

| Formulation | | Parts |
|---|---|---|
| P | Methyl ethyl ketone | 300 |
| | Azo diisobutyronitrile | 0.5 |
| Q | Product from Example 3 | 10 |
| | Methyl methacrylate | 180 |
| | Butyl acrylate | 20 |
| R | Azodiisobutyronitrile | 0.5 |
| | Ethyl acetate | 5 |

A round-bottom flask fitted with a stirrer, condenser and thermometer was employed. The flask was heated with an electric mantle.

Mix P was raised to reflux. After 20 minutes, addition of Mix Q and half of Mix R was started and completed over 2 hours. The remainder of R was added and reflux continued for a further 30 minutes.

The product was a viscous polymer solution, from which the polymer could be separated if required by addition to an excess of methanol followed by washing and drying of the polymer precipitate.

EXAMPLE 12

This Example illustrates the preparation of an aqueous dispersion of particles comprising a copolymer of methyl methacrylate, 2-ethylhexyl acrylate and monomer of structure I as herein defined.

Charges were prepared as follows:

| | | Parts |
|---|---|---|
| A | Water | 614 |
| | Monooleate of polyethylene glycol molecular weight 400 | 2.3 |
| | "Cellosize" WP09L* | 1.4 |
| B | Methyl methacrylate | 342 |
| | 2-Ethylhexyl acrylate | 261 |
| | Monooleate of polyethylene glycol molecular weight 400 | 34.4 |
| | Di-nonyl sodium sulphosuccinate | 4 |
| C | Monomer of structure I** | 6.4 |
| | Water | 15.1 |
| D | Water | 62 |
| | Ammonium persulphate | 2 |
| | Borax | 1.5 |

*"Cellosize" is a Registered Trade Mark for a commercially available hydroxyethyl cellulose.
**Monomer of structure I was made according to Example 1 by reacting an aqueous solution of amino ethyl amidazolidone with an equimolar amount of butylene oxide and then with an equimolar amount of glycidyl methacrylate. In this monomer $A = CH_3CH_2CH(OH)CH_2$— or $CH_3CH_2CHCH_2OH$

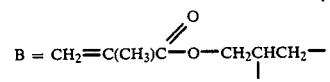

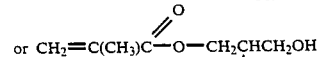

$R_1 = R_2 = -CH_2-CH_2-$

The aqueous charge A, was prepared at 85° C. in a glass reactor (2 liters) with a flange top fitted with lid, stirrer, condenser and thermometer. Monomer mixture could be fed to the reactor at a controlled rate using a small pump and a burette was used to add initiator solution at regular intervals. 32 parts of B and 13 parts of D were added and after a further 45 minutes a further 514 parts of B were added at a constant rate over 2 hours. Over the same time period 30 parts of D was added at the rate of 3 parts per 10 minutes. During the stage the temperature was raised and maintained at 90° C. The remainder of B, all of C and a further 9 parts of D were added over a further 30 minutes, 10 minutes after these additions were completed, the remainder of D was added. After a further 10 minutes the latex was cooled.

The product was a stable, high solids aqueous dispersion of polymer particles in which the polymer comprised 1% of monomer residues of structure II as defined herein.

EXAMPLE 13

This Example is similar to Example 12 except that the monomer of structure I was used as a solution in isopropanol and thus charge C comprised:

|  | Parts |
|---|---|
| Monomer of structure I as defined in Example 12 | 12.8 |
| Isopropanol | 8.7 |

The method used was the same as in Example 12 except that charge C was mixed with the remainder of B prior to the 30 minute addition.

The product was a stable, high solids aqueous dispersion of polymer particles in which the polymer comprised 2% of monomer residues of structure II as defined herein.

EXAMPLE 14

This is a comparative Example in which the polymer dispersions of Examples 12 and 13 are compared with a polymer dispersion ("the dispersion of Example 14") which doe not contain the residues of monomer of structure I.

A stable, high solids, aqueous dispersion of polymer particles was prepared as described in Example 12 but the monomer of structure I was excluded. This dispersion was readily distinguished from the products of Examples 12 and 13 by the following simple test:

A hardboard panel was sprayed with a conventional alkyd undercoat paint; allowed to dry for one week; the sprayed with conventional alkyd; allowed to dry for one week; and then placed in an oven st 70° C. for 7 hours to complete curing. Films of the dispersions from Examples 12-14 were cast onto the alkyd surface using an applicator bar of 8 thou depth and by drying in an oven at 30° C. for 30 minutes. The films were aged for 24 hours at 25° C. Using a sharp blade the films were each cross-hatched using cuts approximately 1 inch long. The panel was soaked in water at 25° C. for 1 hour. Changes in the film appearance were noted. Immediately after the water-soak, surplus water was removed and to each film in turn sticky tape was applied to the film over cross-hatch cuts and the tape ripped sideways. The ease with which the film was removed was noted.

|  | Dispersion of Example No. | | |
|---|---|---|---|
|  | 12 | 13 | 14 |
| Structure I monomer content | 1% | 2% | 0 |
| Observations during water-soak | | | |
| Rapid whitening and swelling. | Slight | None | Considerable. |
| Blister formation. | None | None | Yes |
| Amount of film detached with sticky tape | Partial detachment | None | All detached |

EXAMPLES 15–19

In these Examples, dispersions were prepared as in Example 12 except that different structure I monomers were employed in charge C. The different monomers had been prepared by reacting compounds with aminoethyl imidazolidinone (AEUr) as indicated below:

Example 15: (AEUr/allyl glycidyl ether)/glycidyl methacrylate
Example 16: (AEUr/glycidol)/glycidyl methacrylate
Example 17: (AEUr/glycidyl methacrylate)/glycidyl methacrylate
Example 18: (AEUr/glycidyl "Versatate")/glycidyl methacrylate
Example 19: (AEUr/acrylinitrile/glycidyl methacrylate The products were stable, high solids dispersions of particles of polymer comprising 1% of monomer residues of structure II as defined herein.

EXAMPLE 20

In this Example a dispersion of polymer particles in water was made as follows:

|  |  | Parts |
|---|---|---|
| Charge A | Water | 192 |
|  | Sodium carboxyl methyl cellulose | 2 |
| Charge B | Methyl methacrylate | 17 |
|  | Butyl acrylate | 17 |
|  | Poly(ethylene oxide)/nonyl phenol (average 25 units per molecule) | 1 |
|  | Di-octyl sodium sulphosuccinate | 0.5 |
| Charge C | Monomer structure I as in Example 12 | 1.9 |
|  | Water | 0.5 |
| Charge D | Water | 4.7 |
|  | Potassium persulphate | 2.3 |

Charge A was added to a round-bottom flask (500 ml) fitted with magnetic stirrer and condenser. The flask was positioned in a hot water-bath and the temperature of the charge raised and maintained at 85° C. with stirring, to produce a homogeneous minute free from lumps.

Additions were made as follows:

| Time after Charge A preparation (mins) | Parts of Charge B | Parts of Charge C | Parts of Charge D |
|---|---|---|---|
| 15 | 5.5 | — | 2 |
| 35 | 10 | — | 1 |
| 55 | 10 | — | 1 |
| 70 | 10 | 2.4 | — |
| 80 | — | — | 1 |

| Time after Charge A preparation (mins) | Parts of Charge B | Parts of Charge C | Parts of Charge D |
|---|---|---|---|
| 95 | — | — | 2 |

After a further 15 minutes, the resulting latex was cooled.

The product was an aqueous dispersion of polymer particles in which the polymer comprised approximately 5% of monomer residues of structure II as defined herein.

EXAMPLE 21

This Example describes the preparation of a dispersion of particles comprising a copolymer of styrene, 2-ethylhexyl acrylate and monomer of structure I as defined below.

| | | Parts |
|---|---|---|
| Charge A | Water | 611 |
| | Monooleate of polyethylene glycol molecular weight 400 | 2.3 |
| | "Cellosize" WP09L | 1.4 |
| Charge B | Styrene | 318 |
| | 2-ethylhexyl acrylate | 286 |
| | Monooleate of polyethylene glycol molecular weight 400 | 34.4 |
| | di-nonyl sodium sulphosuccinate | 4.0 |
| Charge C | Monomer of structure I as defined below | 13.1 |
| | Isopropanol | 11.3 |
| Charge D | Water | 62 |
| | Ammonium persulphate | 2 |
| | Borax | 1.5 |

The monomer of structure I was similar to that used in Example 12 but was made by reacting a solution of aminoethyl imidazolidinone in isopropanol (instead of in water as in Example 12 with an equimolar amount of butylene oxide and then with an equimolar amount of glycidyl methacrylate.

The same method was used in Example 12 except that C was mixed with the remainder of B prior to addition to the site of polymerisation.

The product was a stable, high solids dispersion of polymer particles in which the polymer comprised about 2% of monomer residues of structure II as defined herein.

EXAMPLE 22

This Example describes the preparation of a dispersion of a copolymer of vinyl acetate, vinyl "Versatate" and monomer of structure I as defined below, by a method similar to that used in Example 12.

| | | Parts |
|---|---|---|
| Charge A | Water | 533 |
| | Poly(ethylene glycel)/nonyl phenol as in Example 20 | 15.1 |
| | Hydroxyethyl cellulose | 10.8 |
| | di-octyl sodium sulphosuccinate | 3.2 |
| | Sodium bicarbonate | 2.2 |
| Charge B | Vinyl acetate | 551 |
| | *"VeOVa 10" | 138 |
| Charge C | Water | 60 |
| | Ammonium persulphate | 2.2 |
| Charge D | **Monomer of structure I as defined below | 14.5 |
| | Water | 11.2 |

*"VeOVa" is a Registered Trade Mark for a commercially available vinyl "Versatate".

**The monomer of structure I was prepared by reacting an aqueous solution of aminoethyl imidazolidinone with an equimolar amount of glycidol and then with an equimolar amount of glycidyl methacrylate, so that in structure I

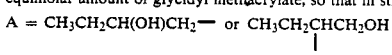

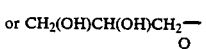

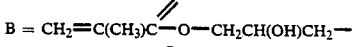

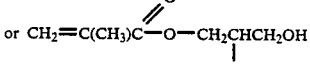

The aqueous charge A was prepared by raising the temperature of A to 60° C. 72 parts of B and 15.5 parts of C were added and the temperature raised to 85° C. After 40 minutes the remainder of B and a further 34 parts of C were metered to the reactor over 4½ hours; during the last 1½ hours of this interval, D was added. After a further 10 minutes, the remainder of C was added. The dispersion was cooled after 10 minutes.

The product was a stable, high solids dispersion of polymer particles comprising a vinyl acetate copolymer containing about 2% of monomer residues of structure II as defined

EXAMPLE 23

This Example describes the preparation of a dispersion in water/methanol of polymer particles comprising a copolymer of methyl methacrylate/butyl acrylate/-methoxy ether of poly(ethylene glycol) monomethacrylate/monomer of structure I as in Example 13.

A round-bottom reactor with flange top and fitted with stirrer, thermometer, nitrogen supply and an up-and-over condenser system was used. The latter was arranged so that distillate from the reactor could be collected and used to dilute the monomer mixtures before returning and dropping into the reactor.

| | | Parts |
|---|---|---|
| Charge A | Water | 315 |
| | Methanol | 466 |
| | Methoxy ether of poly (ethylene glycol) mono methacrylate | 18.7 |
| Charge B | Methyl methacrylate | 26 |
| | Butyl acrylate | 24 |
| | Azodiisobutyronitrile | 1 |
| Charge C | Methyl methacrylate | 214 |
| | Butyl acrylate | 198 |
| | Methoxy ether of poly(ethylene glycol) mono methacrylate | 16 |
| | Methanol | 48 |
| | Azodiisobutyronitrile | 6.7 |
| Charge D | Methyl methacrylate | 46.6 |
| | Butyl acrylate | 42.1 |
| | Monomer of structure I as Example 13 | 11.2 |
| | Isopropanol | 7.1 |
| | Azodiisobutyronitrile | 1.3 |
| Charge E | Azodiisobutyronitrile | 1.6 |

Charge A was added to the reactor and the temperature raised to 65° C. Charge B was added. The temperature was raised to reflux and held for 30 minutes, after which the addition of C was started. This was continued over 3 hours, followed by addition of D over 1 hour. Reflux was continued and after ½ hour 0.8 parts of E were added. The remainder of E was added after a further ½ hour. After another ½ hour interval, the dispersion was cooled. The product was a stable dispersion of polymer particles in a water/methanol medium in which the polymer comprised about 2% of monomer residues of structure II.

EXAMPLE 24

This Example describes the preparation of an initial dispersion in water of polymer particles in which the polymer is a copolymer of methyl methacrylate/2-ethylhexyl acrylate/glycidyl methacrylate. The copolymer of this initial dispersion is subsequently reacted with a secondary amine to introduce monomer residues of structure II.

The apparatus used was the same as in Example 12.

|  |  | Parts |
|---|---|---|
| Charge A | Water | 550 |
|  | Monooleate of poly (ethylene glycol) molecular weight 400 | 2.3 |
|  | "Cellosize" WP09L | 1.3 |
| Charge B | Methyl methacrylate | 315 |
|  | 2-ethylhexyl acrylate | 283 |
|  | Monooleate of poly (ethylene glycol) molecular weight 400 | 34.4 |
|  | di-nonyl sodium sulphosuccinate | 4.0 |
|  | Glycidyl methacrylate | 18.5 |
| Charge D | Water | 62 |
|  | Ammonium persulphate | 2 |
|  | Borax | 1.5 |
| Charge E | A secondary amine made by reacting a solution of amino-ethyl imidazolidinone with an equimolar amount of butylene oxide | 13 |
|  | Water | 31 |

Using A, B, and D a dispersion of polymer particles in water was made employing the method as described in Example 12. The dispersion temperature was adjusted to 60° C. E was added and the temperature held with continuous stirring for 3 hours.

The product was a stable, high solids dispersion of polymer particles in which the polymer included monomer residues of structure II.

EXAMPLE 25

This Example describes the preparation of a dispersion in water of polymer particles comprising a copolymer of methyl methacrylate/2-ethylhexyl acrylate/monomer of structure I as defined below.

The preparation was similar to Examples 12 and 13 except that the monomer composition was different during the addition of the monomer of structure I giving a polymer of lower Tg.

|  |  | Parts |
|---|---|---|
| Charge A | Water | 614 |
|  | Monooleate of poly (ethylene glycol) | 2.3 |
|  | molecular weight 400 |  |
|  | "Cellosize" WP09L | 1.4 |
| Charge B | Methyl methacrylate | 287 |
|  | 2-ethylhexyl acrylate | 196 |
|  | Monooleate of poly (ethylene glycol) molecular weight 400 | 27.5 |
|  | di-nonyl sodium sulphosuccinate | 3.2 |
| Charge C | Methyl methacrylate | 49 |
|  | 2-ethylhexyl acrylate | 72 |
|  | Monooleate of poly (ethylene glycol) molecular weight 400 | 6.9 |
|  | di-nonyl sodium sulphosuccinate | 0.8 |
|  | Monomer of structure I * | 12 |
|  | Isopropanol | 8 |
| Charge D | Water | 62 |
|  | Ammonium persulphate | 2 |
|  | Borax | 1.5 |

(*This monomer was prepared by reacting amino-ethyl imidazolidinone in isopropanol with an equimolar amount of allyl glycidyl ether and then with an equimolar amount of glycidyl methacrylate).

The aqueous charge A was prepared at 81° C. 32 parts of B and 13 parts of D were added. All of B and 36 parts of D were added at a constant rate over 2 hours. During this stage the temperature was raised and maintained at 90° C. All of C and a further 9 parts of D was added at a constant rate over 30 minutes. 10 minutes after these additions were completed, the remainder of D was added. After a further 10 minutes, the latex was cooled. The product was a stable, high solids dispersion of polymer particles in which the copolymer comprised about 2% of monomer residues of structure II as defined herein.

EXAMPLE 26

This Example describes the preparation of two water-based paints in which the binders were a dispersion of polymer particles prepared according to Examples 13 and 14 respectively.

|  |  | Parts |
|---|---|---|
| A | Water | 10.23 |
|  | Hydroxyethyl cellulose | 0.24 |
|  | Amino methyl propanol | 0.08 |
|  | "Tamol" 731 | 0.24 |
|  | "Glascol" | 3.21 |
|  | "Viscalex" VG2 | 1.60 |
|  | Ammonia | 0.16 |
| B | Propylene glycol | 7.00 |
|  | "Tamol" 731 | 0.24 |
|  | Amino methyl propanol | 0.08 |
|  | Titanium dioxide | 21.66 |
| C | Propylene glycol | 2.23 |
| D | "Texanol" ** | 2.01 |

*Commercially available paint additives, "Tamol", "Glascol" and "Viscalex" are Registered Trade Marks.
**Commercially available coalescing agent. "Texanol" is a Registered Trade Mark.

A solution of thickener (A) was made using simple stirring. A millbase (B) was produced using a high speed disperser until the pigment was stably dispersed to a fine particle size and then (C) was added to this. Paints were prepared using the following order and ensuring that complete mixing was achieved at each stage before adding the next component:

| | Parts |
|---|---|
| Dispersion of polymer particles (made as in Example 13 or 14) | 49.0 |
| Water | 2.02 |
| Millbase (B/C) | 31.21 |
| Thickener solution (A) | 15.76 |
| Coalescing agent (D) | 2.01 |

Paints 1 and 2 were prepared using the dispersions of polymer particles from Examples 13 and 14 respectively. The polymer used to prepare Paint 1 included monomer residue of structure II whereas this residue was absent in Paint 2. This was the only difference between the two paints.

Substantial differences in water sensitivity and wet adhesion between the two paints were readily demonstrated by simple tests, as follows:

A hardboard panel was painted with an alkyd undercoat and alkyd gloss as in Example 14. Samples of the two Paints 1 and 2 were applied over the alkyd surface to 8 thou. wet film thickness using a spreader bar. The paints were allowed to dry for 4 hours at 25° C. and 25% relative humidity. The panel was immersed in water at 25° C. for 1 hour and then examined. Paint 2 showed blistering and a slow-recovery (20 minutes) to the original paint hardness. Paint 1 produced no blisters and recovered more rapidly (10 minutes).

In another test the paints were again applied over an alkyd-coated substrate. After curing for 7 days, the films were scribed with a sharp blade with 4 cuts approximately 1 inch long to make an eight-pointed cross. The panels were placed on a "Gardner" washability machine and subjected to the reciprocating action of a nylon bristle brush. The panel was wetted with a standard detergent solution throughout the test. The test was stopped when there was gross loss of film from the area of the scribed cross. With Paint 2 failure was observed after 220 oscillations and was complete after 420 oscillations whereas with Paint 1 no failure was evident after 600 oscillations.

EXAMPLE 27

This Example describes a simple test to show the pronounced difference in adhesive performance between an aqueous dispersion which did not include monomer residue of structure II and a dispersion which did include this residue.

A board was painted with a conventional alkyd solvent-borne undercoat paint and allowed to dry for 1 week. One half of the board was then coated with the dispersion of Example 14 using a paint brush, and the other half coated with the dispersion of Example 13. When dry a second coat of each was applied in similar fashion to the respective halves. After drying for one day, the entire board was overcoated with a conventional solvent-borne gloss paint.

After a further day, sticky tape was pressed onto areas of the painted board. Where the dispersion of Example 14 had been used, it was easy to detach the entire threecoat system from the undercoat showing poor adhesion to that substrate. Where the dispersion of Example 13 had been used it was not possible to raise or detach the paint at all, demonstrating a large improvement in adhesive performance resulting from the presence of the residue of monomer structure II.

We claim:

1. A polymerisable monomer of the structure

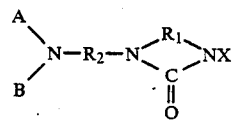

wherein $R_1$ and $R_2$ are the same or different alkylene groups containing 2 or 3 carbon atoms, A is an alkyl group containing 2 to 18 carbon atoms substituted with at least one hydroxyl or cyano group, B is an acryloxyalkyl wherein the alkyl group contains 2 to 18 carbon atoms and is unsubstituted or substituted with a hydroxyl group and X is hydrogen, $C_1$ to 18 alkyl or

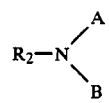

and wherein A and B are each linked to the nitrogen through a carbon atom.

2. A polymerisable monomer of structure

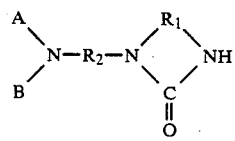

wherein A, B, $R_1$ and $R_2$ are as defined in claim 1.

3. A polymerisable monomer according to claim 1 wherein group B is a substituted propyl group of structure.

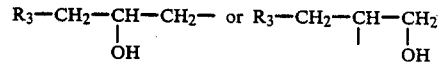

wherein $R_3$ is $CH_2=CH-CO_2-$.

4. A polymerisable monomer according to claim 1 wherein $R_1$ and $R_2$ are both ethylene groups.

5. A polymerisable monomer according to claim 1 wherein A is hydroxybutyl.

6. A polymerisable monomer according to claim 1 wherein A is cyanoethyl.

7. A polymerisable monomer according to claim 1 wherein A is dihydroxpropyl.

* * * * *